United States Patent [19]
Branigan et al.

[11] Patent Number: 5,452,717
[45] Date of Patent: * Sep. 26, 1995

[54] FINGER-COT PROBE

[75] Inventors: Brendan Branigan, Camarillo; Esmaiel Kiani-Azarbayjany, Laguna Niguel, both of Calif.

[73] Assignee: Masimo Corporation, Laguna Hills, Calif.

[ * ] Notice: The portion of the term of this patent subsequent to Aug. 16, 2011 has been disclaimed.

[21] Appl. No.: 253,100

[22] Filed: Jun. 2, 1994

Related U.S. Application Data

[63] Continuation-in-part of Ser. No. 91,873, Jul. 14, 1993, Pat. No. 5,337,744.

[51] Int. Cl.⁶ .................................................. A61B 5/00
[52] U.S. Cl. ......................... 128/633; 128/665; 128/666; 356/41
[58] Field of Search ............................ 128/633, 664–666, 128/886; 356/41

[56] References Cited

U.S. PATENT DOCUMENTS

| | | |
|---|---|---|
| 2,567,926 | 9/1951 | Dunkelberger . |
| 4,321,930 | 3/1982 | Jobsis et al. ............................ 128/633 |
| 4,334,544 | 6/1982 | Hill et al. . |
| 4,621,643 | 11/1986 | New, Jr. et al. . |
| 4,830,014 | 5/1989 | Goodman et al. . |
| 4,867,165 | 9/1989 | Nolles et al. . |
| 4,907,594 | 3/1990 | Muz . |
| 4,928,691 | 5/1990 | Nicolson et al. ........................ 128/633 |
| 5,031,608 | 7/1991 | Weinstein ............................... 128/880 |
| 5,125,403 | 6/1992 | Culp ........................................ 128/665 |
| 5,217,013 | 6/1993 | Lewis et al. ............................ 128/666 |
| 5,337,744 | 8/1994 | Branigan . |

FOREIGN PATENT DOCUMENTS

9216142  10/1992  WIPO .................................... 128/633

Primary Examiner—Lee S. Cohen
Assistant Examiner—Robert L. Nasser, Jr.
Attorney, Agent, or Firm—Knobbe, Martens, Olson & Bear

[57] ABSTRACT

An oximetric sensor probe is movably coupled to a patient's finger to facilitate transillumination and detection of optical energy through a portion of the patient's finger without subjecting the finger to significant deformation. The finger is received within a receptacle having a cup-shaped closed end and an opposite open end that is rolled up upon itself and is adapted to be unrolled longitudinally along the finger to form a tubular enclosure which closely surrounds the finger. An optical source and an optical detector are arranged in spaced axial alignment with each other on opposite sides of the finger so that optical energy transmitted by the source through the finger is received by the detector. The detected light is analyzed to noninvasively determine the saturation of oxygen within the patient's blood. By virtue of the non-adhesive connection between the probe and the finger, decoupling the optical path between the source and detector is minimized in the event that the patient moves his finger during testing. The optical source and optical detector also are separable from the finger cot such that the optical sensor may be reused with another finger cot.

39 Claims, 6 Drawing Sheets

FINGER-COT PROBE

RELATED CASE

This application is a continuation-in-part of application Ser. No. 08/091,873, filed Jul. 14, 1993, now U.S. Pat. No. 5,337,744, issued on Aug. 16, 1994.

BACKGROUND OF THE INVENTION

1. Field of the Invention

This invention relates to an oximetric sensor that is nonadhesively attached to a human digit (e.g., a finger) via an inexpensive, disposable finger cot to analyze the blood of a patient by calculating the concentration of blood constituents (e.g., the saturation level of oxygen in the patient's blood) while minimizing potentially interfering noise artifact signals.

2. Description of Related Art

Electromagnetic energy is often transmitted through or reflected from a medium to determine the characteristics of the medium. In the medical field, optical energy can be transmitted or reflected through human tissue and subsequently measured to determine information about the tissue rather than extracting material from a patient's body for testing. This form of noninvasive measurement can be performed quickly and easily, and has proven to be more comfortable to the patient.

Noninvasive physiological monitoring of body functions is often required when treating a patient. For instance, the available supply of oxygen in the body (i.e., blood oxygenation) is often monitored during surgery. Today this measurement commonly is performed by a noninvasive technique that measures the ratio of incident to transmitted (or reflected) light through a blood-perfused portion of the body, such as, for example, a finger, an ear lobe, or the forehead.

Transmission of optical energy as it passes through the body is strongly affected by several factors. Such factors include the thickness of the tissue through which the energy passes, optical coupling, the optical angle, and the distance between the detector and the source of energy (i.e., the optical path length).

Several parts of the human body are soft and compressible, and therefore are ideally suited to transmit optical energy. For example, a human digit, such as the finger, comprises skin, muscle, tissue, bone, blood, etc. Although the bone is relatively incompressible, the tissue surrounding the bone is easily compressed when an external pressure is applied to the finger. Accordingly, such digits are well suited for the transillumination or transreflection of optical energy for blood monitoring purposes.

Optical probes have been used in the past for both invasive and noninvasive applications. In the typical optical probe, a light emitting diode (LED) is placed on one side of the human tissue while a photodetector is placed on the opposite side. Such conventional optical probes are primarily useful when a patient is relatively motionless and in environments which are characterized by low ambient light.

By way of particular example, one well-known noninvasive measuring device in which an optical probe is used in health applications is the pulse oximeter which measures the pulse rate and the percent of oxygen available in an arterial vessel. Up until the early 1980s, clinicians relied upon arterial blood gas analysis to evaluate gas exchange and oxygen transport within the human body. Although the arterial blood gas test gives valuable information, it only reflects a patient's oxygenation status for one moment in time. On the other hand, pulse oximetry permits a continuous, noninvasive measurement of a patient's arterial oxygen saturation status.

Oximetry is based on the principal that blood hemoglobin absorbs red and infrared light differently when carrying oxygen, in the form of oxyhemoglobin, than when not carrying oxygen, in the form of reduced hemoglobin. Prior oximetric sensors sense the absorption rate of the optical energy by the blood hemoglobin to determine arterial blood oxygen saturation; i.e., the amount of hemoglobin-carried oxygen in relation to the total hemoglobin-carrying capacity.

For this reason, prior oximetric sensor commonly includes a photodetector and a pair of LEDs which emit both red and infrared light. The sensor is packaged in such a way that the LEDs and photodetector are placed on opposite sides of a vascular bed which, in the transillumination case, is usually a finger, ear lobe, or toe. In the reflectance case, the LEDs and the photodetector are placed side by side over a vascular bed, usually the forehead, but separated by a barrier which blocks light from reaching the detector without first passing through the tissue sample. When properly positioned, the LEDs emit known wavelengths of both red and infrared light for transmission or transreflection through the vascular bed for receipt by the detector.

The photodetector produces a signal in response to unabsorbed light passed through the vascular bed to the detector. This signal conventionally is converted to digital form and then supplied to a computer or microprocessor which computes the ratio of red light to infrared light absorption. The absorption data is then utilized to determine the arterial blood oxygen saturation values which then may be displayed on a monitor or a strip chart. Because the light that is directed into the vascular bed also is at least partially absorbed by the nearby tissue and bone material, the oximeter typically utilizes the alternating bright and dim signals caused by arterial pulsations to further clarify the presence of both reduced hemoglobin and oxyhemoglobin, as known in the art.

Prior pulse oximeters provide health care providers with the ability to assess second to second changes in a patient's arterial oxygen saturation. This enables possible intervention before hypoxemia occurs. (Hypoxemia results from lack of oxygen in the blood which can lead to brain damage or even death.) The health care provider also is able to evaluate the patient's response to treatment on a continuous basis.

Initially utilized in the operating room, pulse oximetry is becoming increasingly common in other parts of the hospital, including emergency rooms, adult and neonatal intensive care units, and post anesthesia care units. It is expected that pulse oximeters will also find their way into the general ward and even outside the hospital by medical emergency technicians and private physicians. It is in these new areas that the prior optical probes have proven to be inadequate due to patient movement and the relatively noisy environments in which they are used.

One conventional optical sensor that is adhesively attached to a patient's finger is disclosed in U.S. Pat. No. 4,830,014, issued May 16, 1989, to Goodman et al. In its pre-application configuration, the sensor has a planar 'T' shape with an adhesive layer covering an entire side. The area of the sensor which is intended to cover the curved surface of the finger is narrowed so as to provide less stability at the fingertip. The probe includes a complex, layered structure formed by a plurality of juxtaposed layers joined together by interposed layers of adhesive. A first layer includes apertures through which a light source and an optical detector communicate with each other. Another layer firmly engages (i.e., adheres to) the patient's finger. The sensor consequently moves with the finger. The configuration of this sensor also demands that the light source and the detector must be aligned precisely with the corresponding apertures to insure that light will pass through the apertures and between the source and the detector.

Prior optical sensors, such as that disclosed by Goodman, suffer from several drawbacks. For instance, such sensors which adhesively attach to the patient's skin, are susceptible to decoupling when the patient's finger is moved erratically. That is, the occasional movement of the finger commonly places the skin on one side of the finger in tension and places the skin on the opposite side of the finger in compression. The source and detector, which are attached to the skin on opposites sides of the finger, thus are moved as the skin is placed in tension or compression, and such movement can result in misalignment between the source and the detector and/or can change the radiation angle between the source and detector. The movement can also change the optical path length between the source and the detector. As a result, the misalignment and/or increase in the path length produce motion artifact signals, which are unpredictable and thus uncompensatable, and which consequently causes the output signal from the detector to be difficult to interpret and not representative of the amount of the transilluminated or transreflected light.

Another known optical sensor is described in U.S. Pat. No. 5,125,403 issued Jun. 30, 1992 to Culp. A woven tube which is folded partially inside itself secures a side-folding light source and detector structure about a patient's finger tip. The finger engages the side-folding structure and pushes it inside the woven tube causing the tube to begin sliding inside out. However, the woven tube is unstable, tending to reverse its inside out movement. Moreover, the side-folding structure can slide off the tip of the finger thereby requiring the entire assembly to be refolded and refitted onto the finger. Flexing the finger can also cause disengagement, and the woven structure does not sufficiently act to straighten the finger after the finger has been flexed.

SUMMARY OF THE INVENTION

The present invention relates to a low-noise oximetric finger-cot probe. The finger-cot probe is nonadhesively attached to a human digit (e.g., a finger) so that the digit will remain essentially nondeformed if the patient moves his or her finger slightly. This advantageously avoids the shortcomings associated with conventional optical sensors that are adhesively bonded to a finger and, as described above, are undesirably susceptible to a displacement and a decoupling of the optical source relative to the detector if the patient moves his digit. By virtue of the nonadhesive coupling between the oximetric sensor and the digit, the optical path is preserved and the angular displacement of the detector relative to the sensor is reduced.

In accordance with one aspect of the present invention, there is provided a sensor probe for analyzing at least one characteristic of tissue. The sensor probe comprises a sensor comprising at least one source of electromagnetic energy and at least one detector of electromagnetic energy. A carrier supports the sensor and has a body with sufficient flexibility to at least partially surround a portion of the tissue. The sensor source and sensor detector are arranged on the carrier relative to each other so as to transmit electromagnetic energy between each other and through the tissue, with the carrier positioned on a portion of tissue. The probe also includes a generally elastic, disposable sheath, which has a first end and a second end. The first end of the sheath is coupled to the carrier. The second end of the sheath has a tubular shape and is rolled upon itself. The second end is also adapted to be unrolled towards the carrier, such that the sheath surrounds at least a portion of the carrier with the carrier positioned on the portion of tissue.

In preferred embodiment, the first end of the sheath is separably attached to the carrier, preferably by a releasable connector positioned between the carrier and the sheath. The releasable connector desirably is a snap-connector, a hook-and-loop connector, a button, a pin, a clip or a similar type of connector, which quickly and easily releasably secures the carrier to the elastic sheath.

In accordance with another aspect of the present invention, there is a provided a sensor probe for analyzing at least one characteristic of tissue. The sensor probe comprises a sensor having at least one source of electromagnetic energy and at least one detector of electromagnetic energy. The sensor probe also includes a generally elastic sheath having a first end and a second end. The first end is configured to capture at least a portion of the tissue to be analyzed. The second end has a generally tubular shape which is rolled upon itself and is adapted to be unrolled over the tissue. The sensor is coupled to the sheath proximate to the first end and is arranged within the sheath such that the sensor source and a sensor detector transmit electromagnetic energy between each other and through the tissue with the sheath positioned over the tissue.

In accordance with a preferred method of analyzing at least one characteristic of tissue, a source and a detector of electromagnetic energy are provided. The source and detector are interconnected and are separably attached to a securement sheath. The source of electromagnetic energy is positioned against the tissue, and the detector of the electromagnetic energy is likewise positioned against the tissue. The sheath is unrolled over the tissue and the source and detector of electromagnetic energy to surround and secure the source and detector to the tissue. Electromagnetic energy is transmitted through the tissue and is received by the detector. The detector generates a signal indicative of the tissue characteristic that is to be analyzed. The sheath is then unrolled off the tissue and disconnected from the source and the detector of the electromagnetic energy.

BRIEF DESCRIPTION OF THE DRAWINGS

These and other features of the invention will now be described with reference to the drawings of preferred embodiments which are intended to illustrate and not to limit the invention, and in which.

DETAILED DESCRIPTION OF PREFERRED EMBODIMENTS

Figure 1:
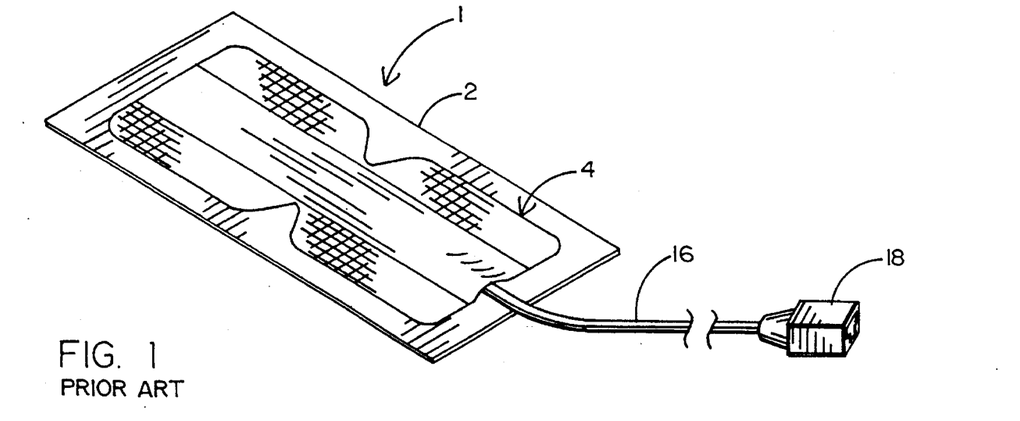
FIGS. 1–3 illustrate a conventional oximeter probe.
Figure 2:
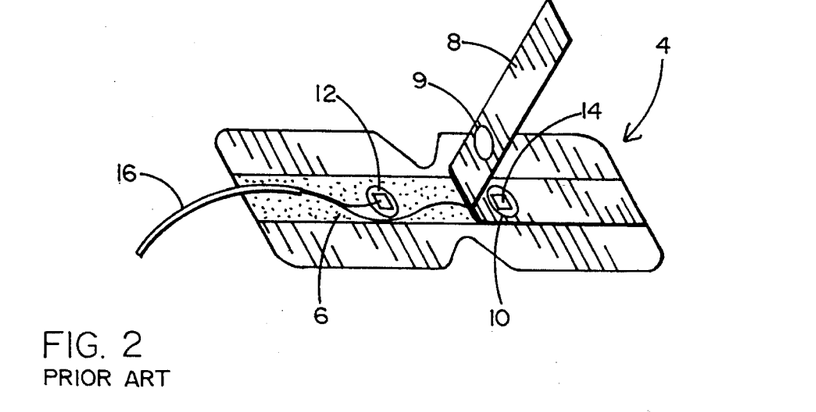
Figure 3:
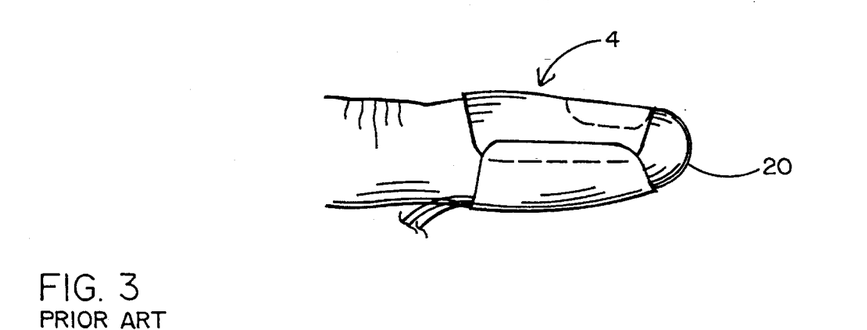

FIGS. 1–3 illustrate a known oximeter probe 1 that is used to monitor blood oxygenation levels in blood-perfused tissue, such as at the tip of a finger. With reference to FIG. 1, the prior oximeter probe 1 includes a release layer 2, which carries a removable retaining bandage 4 (individually shown in FIG. 2) that is adhesively bonded to the release layer 2. As seen in FIG. 2, a relatively thin adhesive hold-down surface 6 extends longitudinally down the middle of the retaining bandage 4. A flexible web 8 covers the hold-down surface 6. The web 8 contains a pair of axially spaced openings 9, 10 formed therethrough. A clear, transparent (e.g., thin plastic) material preferably covers each of the openings 9, 10.

As seen in FIG. 2, the retaining bandage 4 carries an optical source 12 and an optical detector 14. The optical source 12 conventionally is a pair of light emitting diodes (LEDs). The optical source 12 and the optical detector 14 are bonded to bandage 4 at the hold-down surface 6 and are received within the openings 9, 10 of the web 8 when the web 8 is secured against the hold-down surface 6. Wire are attached to each LED of the optical source 12 and to the optical detector 14. The wires are surrounded by an outer protective casing 16 that terminates at a conventional plug 18. The plug 18 connects to a conventional controller (not shown), which supplies signals to and receives signals from the optical source 12 and the optical detector 14.

The face (i.e., the medial surface) of the bandage 4 is covered with adhesive to permit the bandage 4 to be removably attached to a patient's finger or other digit. That is, as best shown in FIG. 3, the bandage 4 is tightly wrapped around a patient's finger 20 so that the optical source 12 and the optical detector 14 are aligned with each other on opposite sides of the finger 20. In this manner, the optical detector can receive optical signals transmitted through the patient's finger 20 by the LEDs of the optical source 12. After monitoring is complete, the retaining bandage 4 is removed from finger 20 and discarded.

Because the bandage 4 is tightly affixed around the patient's finger 20, the adhesively backed retaining bandage 4 is unforgiving in the event that the patient moves his finger during testing. That is, as described above, with the finger held in compression, even slight movement during monitoring tends to decouple the optical source 12 and the detector 14 and causes the optical path length to vary. Such probe movement introduces measurement error called motion artifact errors. Thus, the signal derived from the oximeter probe 1 may be erratic and unreliable under some conditions.

FIGS. 4–11 illustrate a disposable, self-adhering finger-cot probe 21 configured in accordance with a preferred embodiment of the present invention. The finger-cot probe 21 is designed to reduce motion artifact errors in the monitoring signal, as well as to reduce possible noise artifact signals from spurious light (i.e., light from sources other than the sensor 23).

Figure 4:
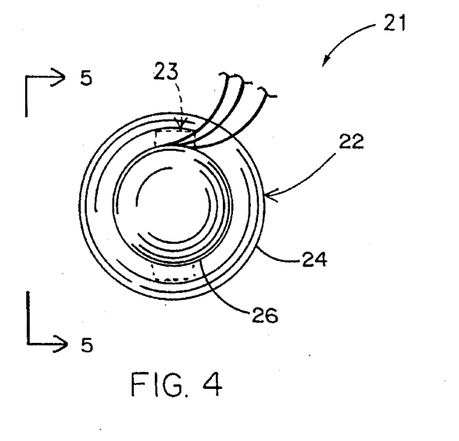
FIG. 4 is a front elevational view of a finger-cot probe in accordance with an embodiment of the present invention.
Figure 5:
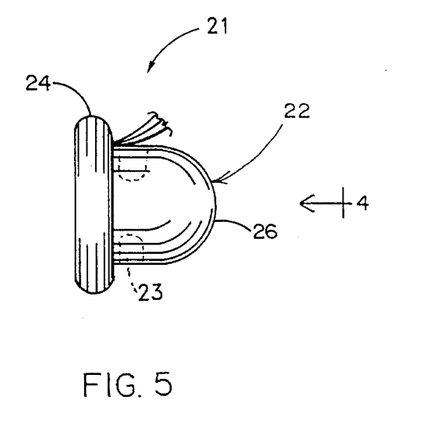
FIG. 5 is a side elevational view of the finger-cot probe of FIG. 4 as seen in the direction of line 5—5.
Figure 6:
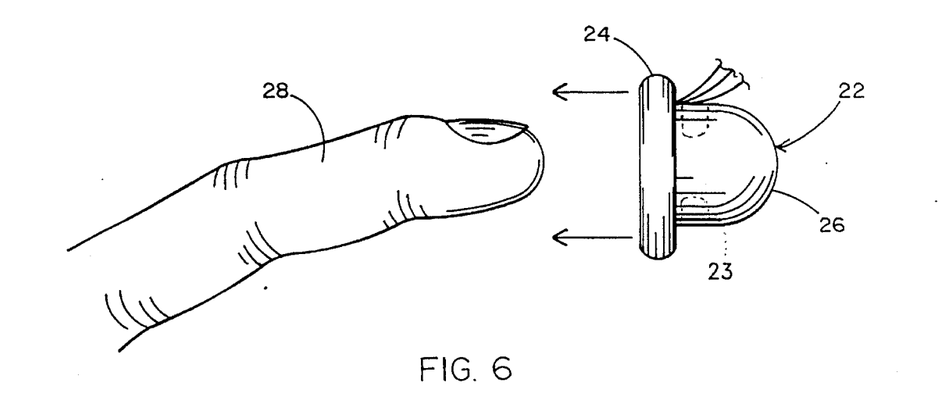
FIGS. 6 and 7 schematically illustrate the steps by which the finger-cot probe of FIG. 4 is applied to a finger of a patient.

With reference to FIG. 4, the present finger-cot probe 21 principally comprises a compact finger cot 22 and a sensor 23. The finger cot 22 is configured to be quickly and easily attached to and removed from a patient's finger or other digit without the need of adhesives or other uncomfortable securing means, such as those common to conventional oximeter probes. It also is understood that the present probe 21 may be used in other blood-perfused body locations in addition to a digit.

In the pre-application configuration illustrated in FIGS. 4–7, the finger cot 22 includes an open proximal end 24 that is rolled upon itself and a closed distal end 26. The closed distal end 26 of finger cot 22 has a cup-shaped configuration to receive the tip of a patient's finger 28.

The finger cot 22 desirably is formed from a thin elastic sheath that preferably is opaque to ambient light, and more preferably is opaque to spurious light of a wavelength within the range detectable by the sensor 23.

Figure 7:
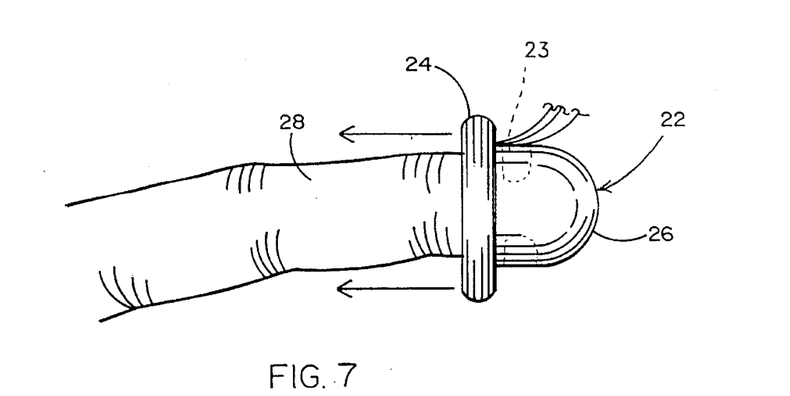

With the patient's finger 28 located at the cup-shaped distal end 26 (as illustrated in FIG. 7), the rolled proximal end 24 is pulled proximally and unrolled longitudinally over the patient's finger 28, so as to form a generally tubular sleeve. The sleeve of the proximal end 24 desirably surrounds the circumference of the finger 28 to form a relatively close fit without fixedly attaching the sensor 23 to the tissue and without significantly compressing the tissue. Thus, the size (circumferentially and longitudinally) of the finger cot 22 should be configured in various sizes to fit a variety of sizes of fingers or other digits, depending upon the age, size, and maturity of the patient.

Figure 8:
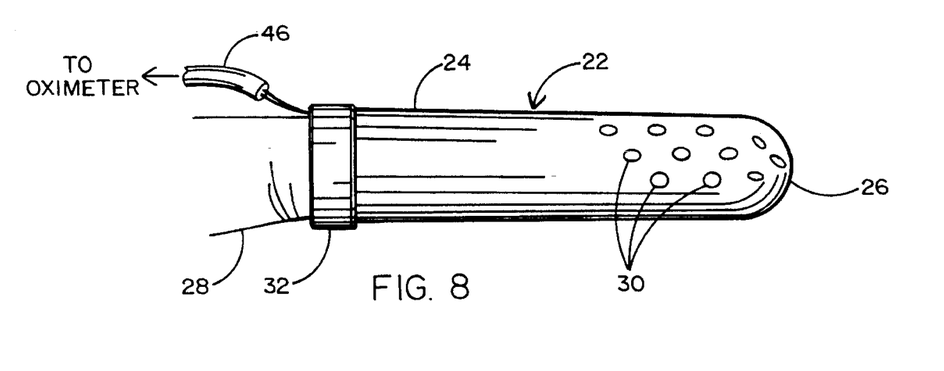
FIG. 8 is a side elevational view which shows the finger-cot probe of FIG. 7 fully applied to the patient's finger.

With reference to FIG. 8, the finger cot 22 may include a series of holes 30 through the sheathing material to increase air flow to the finger 28 for the purpose of maximizing comfort.

When the proximal end 28 is pulled proximally so as to be fully unrolled along the patient's finger 28, the finger cot 22 terminates at a relatively thick peripheral cuff 32. The inner diameter of the cuff 32 is slightly smaller than that of the sleeve so as to apply sufficient pressure to enhance the self-attachment of finger cot 22 to the finger 28 without adhesive or other securing means.

Figure 9:
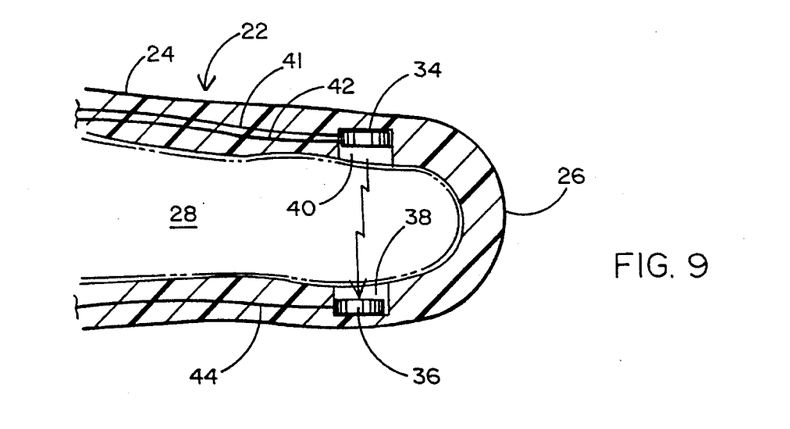
FIG. 9 shows a partial side sectional view of the finger-cot probe of FIG. 8.

With reference to FIG. 9, the sensor 23 is shown with the finger cot 22 unrolled and positioned on the tip of a patient's finger 28. The sensor 23 includes an optical source 34 and an optical detector 36 arranged in spaced optical alignment with one another at the distal end 26 of the finger cot 22 to transilluminate the patient's finger 28 from opposite sides. In the illustrated embodiment, the optical source 34 preferably is a pair of light emitting diodes (LEDs), only one of which is shown in FIG. 9.

Both the optical source 34 and the optical detector 36 are recessed within respective cavities 38, 40 formed in the finger cot 22 to prevent contact between the tissue of the patient's finger and the optical source 34 and the optical detector 36. The patient's tissue, when slightly compressed by the finger cot distal end 26, may be received within either cavity 38, 40, but the tissue does not directly contact the optical source 34 or the optical detector 36 because of the recess depth.

An optional viscous coupling medium, such as an oil or gel, which has an index of refraction which corresponds to that of the patient's skin, desirably fills the cavities 38, 40 to couple the optical source 34 and the optical detector 36 to the patient's tissue. The optical coupling medium remains in contact with the tissue as the patient moves his or her finger. This movement, however, does not move the optical source 34 and sensor 36, and therefore the movement of the finger does not substantially alter the optical coupling or the path length between the source 34 and the detector 36.

As seen in FIG. 9, electrically conductive wires 41, 42 are connected to the LEDs which form the optical source 34. Another electrically conductive wire 44 is connected to the optical detector 36. The wires 41, 42, 44 from the optical source 34 and the detector 36 extend longitudinally through the proximal end 24 of the finger cot 22 to be aligned side by side one another and surrounded by an electrically insulating outer protective casing or sleeve 46 (see FIG. 8) as the wires exit the finger cot 22. The outer sleeve 46 carries the wires 41, 42, 44 to a suitable controller and signal processing means (not shown), which is briefly described below.

Figure 10:
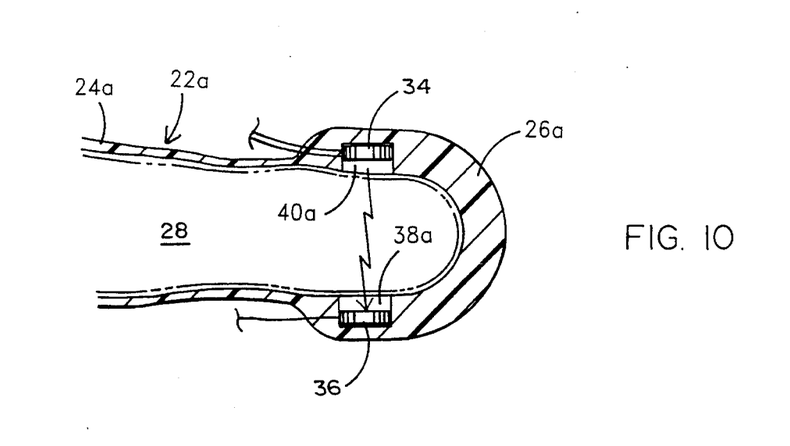
FIG. 10 shows a partial side sectional view of a modified form of the finger-cot probe in accordance with another embodiment of the present invention.

FIG. 10 shows a finger cot 22a that is a modified form of the finger cot 22 illustrated in FIGS. 4–9. For ease of discussion, like reference numerals with an "a" suffix have been used to indicate like components of the two embodiments. While the proximal and distal ends 24a, 26a of the finger cot 22a are of uniform thickness, the distal end 26a of finger cot 22a is thicker than the proximal end 24a of the finger cot 22a. This variation in thickness has been found to make the finger cot 22a easier to roll into the compact, pre-application configuration illustrated in FIGS. 4 and 5.

FIGS. 11–15 show a finger-cot probe 50 according to a further embodiment of the present invention. The probe 50 includes a generally planar protective backing or carrier 52 which is preferably formed from a flexible material (e.g., plastic). A finger cot 54 is attached to the backing 52 at approximately the midpoint of the protective backing 52.

Figure 12:
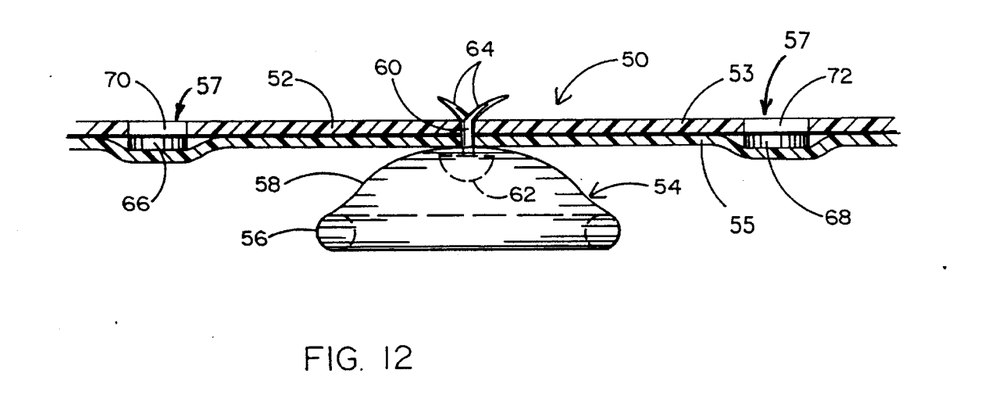
FIG. 12 is a partial cross-sectional view of the finger-cot probe of FIG. 11 with a permanent connector taken along line 12—12 of FIG. 11.

With reference to FIG. 12, the finger cot 54, in its pre-application configuration, includes an open proximal end 56 that is rolled upon itself and a closed, cup-shaped distal end 58. As represented by phantom lines in FIGS. 12 and 13, the proximal end 56 is rolled so as to lie inside the finger cot 54.

The finger cot 54 desirably is manufactured from a thin, elastic sheath that is generally opaque to ambient light, and more preferably is opaque to spurious light of a wavelength within the range detected by the sensor 57.

The finger cot 54 can be either removably or permanently secured to the protective backing 52. Although either form of attachment interconnects the finger cot 54 and the backing 52 equally well, it is preferred that the finger cot 54 be separately attached to the protective backing 52 so that the sensor 57 and backing 52 of the probe 50 can be reused, as discussed below.

Figures 13, 14:
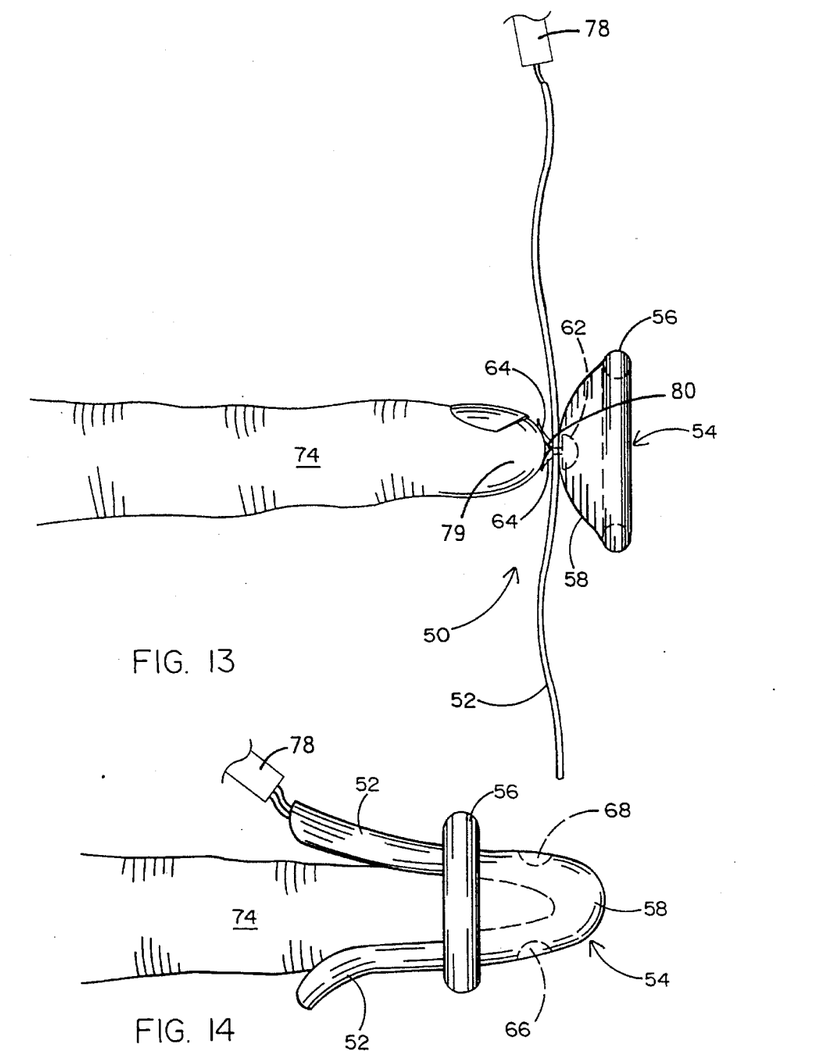
FIGS. 13 and 14 substantially illustrate the steps by which the finger-cot probe of FIG. 11 is applied to a finger of a patient.

FIG. 12 illustrates the finger cot 54 permanently attached to the protective backing 52 by means of a pin 60. The pin 60 has a narrow body, a relatively wide head 62 at one end of the body, and a pair of flexible legs or ties 64 at the opposite end of the body. The pin 60 extends through both the protective backing 52 and the distal end 58 of finger cot 54. The pin head 62 connects the finger cot 54 to one side of the backing 52 with the flexible legs 64 projecting beyond from the opposite side of the backing 52. The legs 64 are bent against the backing 52 and secured (e.g., sewn) to the backing 52 for reliably securing the finger cot 54 to the backing 52. In this position, the legs 64 also serve as a target toward which the patient's finger is aimed when the finger cot 54 is applied, as shown in FIG. 13 and discussed below.

Figure 16:
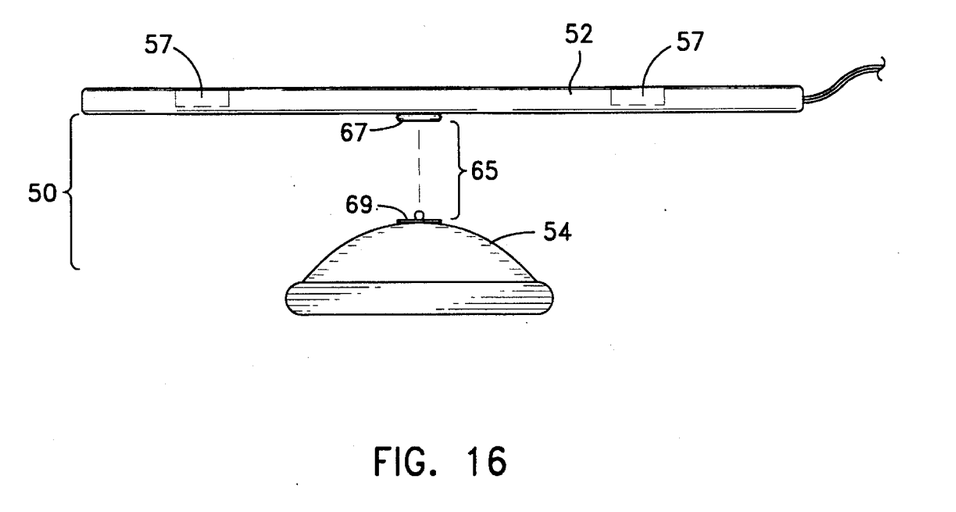
FIG. 16 illustrates a side elevational view of the finger-cot probe of FIG. 11 with a separable connector.

FIG. 16 illustrates the finger cot 54 separately attached to the protective backing 52 by means of a releasable connector 65. In the illustrated embodiment, the removable connector 65 desirably is a conventional snap-type connector; however, it is understood that other types of removable connectors, such as, for example, buttons, hook-and-loop fasteners (i.e., VELCRO®), pins, clips and like detachable couplers could be used equally as well. The snap 65 includes a receptacle element 67 attached to the protective backing 52 and a stud element 69 attached to the finger cot 54. Of course, the orientation of these snap connector components 67, 69 could be reversed.

The releasable attachment between the finger cot 54 and the probe backing 52 allows the sensor portion (i.e., the backing 52 and the optical sensor 57) of the probe 50 to be reused, thus reducing the overall cost of the probe 50. One sensor 57 may be used several times, where the cot 54 is replaced after each use.

Figure 11:
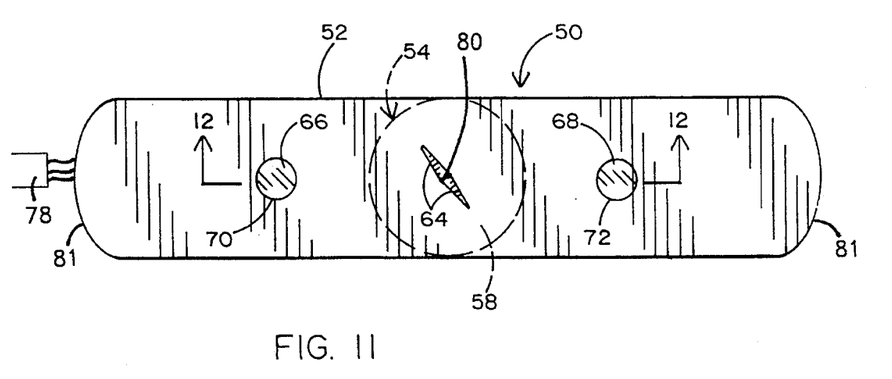
FIG. 11 is a top plan view of a finger-cot probe in accordance with a further embodiment of the present invention.

While the optical source 34 and detector 36 of the finger-cot probe of FIGS. 4–10 were included as an integral part of the finger cot 22, the finger-cot probe 50 of the present embodiment (best seen in FIG. 12) includes an optical source 66 (e.g., a pair of LEDs) and an optical detector 68 which are separated from the finger cot 54. As seen in FIGS. 11 and 12, the optical source 66 and the optical detector 68 are retained at opposite ends of the protective backing 52. The optical source 66 and detector 68 are recessed within respective cavities 70, 72 to prevent contact with the patient's tissue. In this manner, as discussed above, the optical coupling and path length between the optical source 66 and detector 68 are preserved in the event that the patient's finger is moved and/or the tissue is compressed during monitoring.

Figure 15:
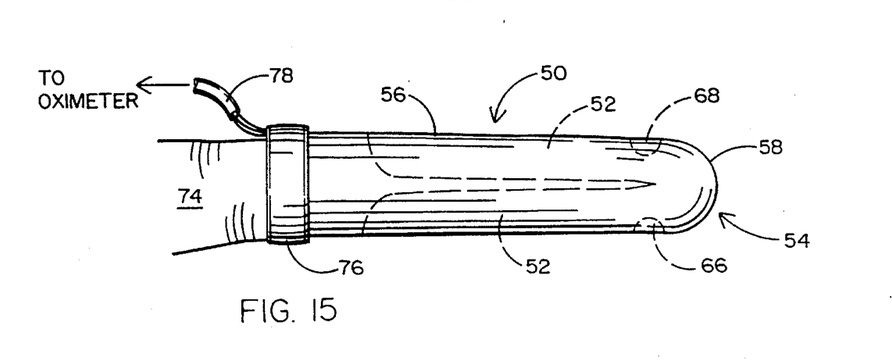
FIG. 15 is a side elevational view which shows the finger-cot probe of FIG. 14 fully applied to the patient's finger.

With reference to FIG. 12, the protective backing 52 of probe 50 may be formed by a top layer 53 and a bottom layer 55 of flexible material to facilitate the formation of the cavities 70 and 72. The optical source 66 and detector 68 are carried by the bottom layer 55, while the cavities 70, 72 are formed in the top layer 53 in axial alignment with the source 66 and the detector 68. Electrically conductive wires (not shown) extend through the finger-cot probe 50 at the interface between the top layer 53 and the bottom layer 55 and connect the source 66 and the detector 68 to a conventional controller and signal processor (not shown). As seen in FIG. 15, an electrically insulating outer protective casing or sleeve 78 desirably surrounds the wires as they exit the probe 50.

As seen in FIG. 11, the sensor source 66 and the sensor detector 68 are arranged on the protective backing 52 so as to be an equal distance from the center or midpoint 80 of the protective backing 52 (i.e., the point at which the finger cot 54 is attached). In the illustrative embodiment, the distance between the source 66 or the detector 68 and the midpoint 80 is less than the distance between the sensor source 66 or the sensor detector 68 and a longitudinal end 81 of the protective backing 52. Both the sensor 66 and detector 68 are exposed on the medial side of the protective backing 52 which is juxtaposed against the tissue to be analyzed, as discussed below.

FIGS. 13–15 illustrate the steps for applying the finger-cot probe 50 to a patient's finger 74 from the pre-application rolled configuration, shown in FIG. 13, to the unrolled, extended configuration, shown in FIG. 15. The patient's finger tip 79 is first placed at the midpoint 80 of the backing 52. For this purpose, the backing 52 preferably includes a target located at the midpoint 80. The target may be the extended legs 64 of the pin 60 or may be indicia marked on the medial side of the backing 52 as well. In the illustrated embodiment, the patient's finger tip 79 is placed on the target formed at the intersection of the flexible legs 64 of the pin 60 opposite the unrolled distal end of finger cot 54. A small amount of adhesive can be applied at the midpoint 80 (e.g., applied to the legs 64) to hold the finger 74 against the midpoint 80 during application of the finger cot 54. The unrolled proximal end 56 of finger cot 54 is then pulled toward the finger 74 and unrolled over the cup-shaped distal end 58 of the finger cot 54. The distal end 58 is inverted in this process to surround the patient's finger tip 79. The continued rearward movement of the proximal end 56 unrolls the sleeve over the protective backing 52. The sleeve urges the opposite medial sides of the backing 52 toward each other and against the respective sides of the finger 74.

In the fully unrolled and applied condition, as illustrated in FIG. 15, the protective backing 52 is bent and retained around the finger 74 in a manner that the optical source 66 and the optical detector 68 are held in spaced optical alignment with each other on opposite sides of the finger 74 so that the finger may be transilluminated. The fully unrolled finger cot 54 terminates at a relatively thick peripheral cuff 76, which applies sufficient pressure to hold the finger cot 54 to the finger 74.

The optical detectors 36, 68 used with the above-described finger-cot probes 21, 50 are responsive to light absorption from the transillumination of the patient's muscle tissue. The output signals provided by the detector 36, 68 can be processed for the purpose of enabling health care providers to analyze the patient's blood by noninvasively calculating the concentration of blood constituents. The output signals from the detectors 36, 68 also may be converted before processing, as known in the art.

In the illustrated embodiments, the output signals derived from the optical detectors 36, 68 can be used to provide a reliable indication of the percentage saturation of oxygen (i.e., the oxygenation level) within the patient's blood. For this purpose, a pulse oximeter (not shown) energizes the optical source 66 to emit two signals that have different wavelengths, one of which is typically red and the other of which is typically infrared. The two signals alternately pass through the patient's fingertip 79. The signals are measured by the optical detector 68 which in turn produces two output signals. The pulse oximeter processes the two output signals from the detector 68 to determine the amount of oxygen available to the body. This information is evaluated to derive the saturation of oxygenated hemoglobin in the blood comprising both oxygenated and deoxygenated hemoglobin.

One pulse oximeter, which is especially suitable for use with the present finger-cot probes 21, 50, is described in co-pending U.S. Patent application Ser. No. 07/672,890, filed Mar. 21, 1991, and assigned to the Assignee of this patent application. The teachings of Patent application Ser. No. 672,890 relating to pulse oximetry are herein incorporated by reference. It is to be understood, however, that this oximeter is given for purposes of example only, and other types of pulse oximeters may be used as well for processing the output signals from the optical detectors.

Once monitoring is complete or is no longer required, a nurse or like health-care provider removes the probe 50. The nurse rolls the cuff 76 towards the end 79 of the finger 74 to expose the protective backing 52. The nurse desirably rolls the finger cot 54 completely off the end 79 of the patient's finger 74 to expose the interconnection between the finger cot 54 and the backing 52. Where the cot 54 and backing 52 are releasably attached, the nurse may unsnap or otherwise disconnect the finger cot 54 from the backing 52. The finger cot 54 can then be disposed, and the sensor can be sterilized and later reused with a new finger cot 54.

It will be apparent that while preferred embodiments of the invention have been shown and described, various modifications and changes may be made without departing from the true spirit and scope of the invention. For example, although the finger-cot probes herein have been described as having particular use with a patient's finger, it is expressly understood that the teachings of this invention are also applicable to any other human digit or suitable palpable tissue area. Additionally, while the optical detectors herein have been described as being responsive to the transillumination of human tissue, it also is understood that the optical detectors may be suitably located to be responsive to transreflectance, as well. Accordingly, the scope of the invention is intended to be defined only by the claims that follow.

What is claimed is:

1. A sensor probe for analyzing at least one characteristic of tissue, comprising:

a sensor including at least one source of electromagnetic energy and at least one detector of electromagnetic energy;

a carrier supporting said sensor and having a body which is sufficiently flexible to at least partially surround a portion of the tissue, said sensor source and said sensor detector being arranged on said carrier relative to each other so as to transmit said electromagnetic energy between each other and through the tissue with said carrier positioned on the portion of tissue; and a generally elastic sheath having a first end and a second end, said first end being coupled to said carrier and said second end having a generally tubular shape which is rolled upon itself through at least two revolutions in a first position, said second end adapted to be unrolled from said first position through at least two revolutions toward and over said carrier to a second position in which said sheath surrounds at least a portion of said carrier with the carrier positioned over the portion of tissues.

2. The sensor probe of claim 1, wherein said sensor source and said sensor detector are arranged on the carrier so as to be generally opposite each other with said carrier positioned on the portion of tissue to transmit said electromagnetic signal directly through the tissue.

3. The sensor probe of claim 1, wherein said first end includes an arcuately shaped surface configured to receive a portion of said tissue.

4. The sensor probe of claim 1, wherein said sensor source is an optical source and said sensor detector is an optical detector.

5. The sensor probe of claim 4, wherein said electromagnetic energy emitted by said optical source has wavelengths corresponding to both red and infrared light.

6. The sensor probe of claim 1, wherein said sensor source and said sensor detector are positioned within said carrier so as to be recessed from a medial surface of said carrier which contacts the portion of the tissue.

7. The sensor probe of claim 1, wherein said sheath is formed of a material which is opaque to at least some wavelengths of electromagnetic energy.

8. The sensor probe of claim 7, wherein said sheath is formed of a material opaque to at least red and infrared wavelengths of light.

9. A sensor probe for analyzing at least one characteristic of tissue, comprising:
   a sensor including at least one source of electromagnetic energy and at least one detector of electromagnetic energy;
   a carrier supporting said sensor and having a body which is sufficiently flexible to at least partially surround a portion of the tissue, said sensor source and said sensor detector being arranged on said carrier relative to each other so as to transmit said electromagnetic energy between each other and through the tissue with said carrier positioned on the portion of tissue; and
   a generally elastic sheath having a first end and a second end, said first end being coupled to said carrier and said second end having a generally tubular shape rolled upon itself, said second end adapted to be unrolled toward and over said carrier such that said sheath surrounds at least a portion of said carrier with the carrier positioned over the portion of tissue; and
   a releasable connector positioned between said carrier and said sheath to separably attach said carrier to said sheath.

10. The sensor probe of claim 2, wherein said releasable connector is selected from a group consisting of a snap-connector, a hook-and-loop connector, a button, a pin, and a clip.

11. The sensor probe of claim 9, wherein said sensor source and said sensor detector are arranged on the carrier so as to be generally opposite each other with said carrier positioned on the portion of tissue to transmit said electromagnetic signal directly through the tissue.

12. The sensor probe of claim 9, wherein said sensor source is an optical source which emits light of both red and infrared wavelengths, and said sensor detector is an optical detector which detects light of both red and infrared wavelengths.

13. The sensor probe of claim 9, wherein said sensor source and sensor detector are positioned within said carrier so as to be recessed from a medial surface of said carrier which contains said portion of tissue.

14. The sensor of claim 13, additionally comprising coupling medium positioned within cavities defined between said medial surface of said carrier and said source or said detector, said coupling medium having an incident of refraction substantially equal to that of the tissue.

15. The sensor probe of claim 9, wherein said sheath is formed of a material which is opaque to at least some wavelengths of electromagnetic energy.

16. The sensor probe of claim 15, wherein said sheath is formed of a material opaque to at least red and infrared wavelengths of light.

17. The sensor of claim 9, wherein said source and said detector are arranged on said carrier such that the distance between said source or said detector to the center of said carrier is less than the distance between said source or said detector to a longitudinal end of said carrier.

18. A sensor probe for analyzing at least one characteristic of tissue comprising:
   a sensor having at least one source of electromagnetic energy and at least one detector of electromagnetic energy; and
   a generally elastic, tubular sheath having a first end and a second end, said tubular sheath adapted to be extended from a compact state, in which said first and second ends are separated by a first distance, to an extended state, in which said first and second ends are separated by a second distance, said second distance being at least twice as long as said first distance, said sheath covering a portion of the tissue in said extended state, said sensor coupled to said sheath proximate to said first end and arranged such that said source and said detector transmit electromagnetic energy between each other and through the tissue with the sheath positioned over the portion of tissue in said second state.

19. The sensor probe of claim 18 additionally comprising a generally elastic cuff attached to said sheath, said cuff having a diameter of a size smaller than a diameter of said second end of said sheath.

20. The sensor probe of claim 18, wherein said first end of said sheath carries said sensor.

21. The sensor probe of claim 18 additionally comprising a carrier which supports said sensor and has a body which is sufficiently flexible to surround a portion of the tissue, said sensor source and said sensor detector being arranged on said carrier relative to each other so as to transmit said electromagnetic energy between each other and through the tissue with the carrier positioned on the portion of the tissue, said carrier being configured so as to be interposed between said sheath and said tissue with said sheath positioned over the tissue.

22. The sensor probe of claim 21, wherein said carrier is coupled to said elastic sheath.

23. The sensor probe of claim 22, wherein said carrier is separably attached to said first end of said sheath.

24. The sensor probe of claim 23 additionally comprising a releasable connector positioned between said carrier and said first end of said sheath to separably interconnect said carrier and said sheath.

25. The sensor of claim 21, wherein said source and said detector are arranged on said carrier such that the distance between said source or said detector to the center of said carrier is less than the distance between said source or said detector to a longitudinal end of said carrier.

26. The sensor of claim 21, wherein said carrier comprises first and second cavities which receive said source and said detector, respectively, so as to position said source and said detector away from the tissue over which the carrier covers.

27. The sensor of claim 26 additionally comprising coupling medium positioned within said cavities between a medial surface of said carrier and said source and said detector, said coupling medium having an incident of refraction substantially equal to that of the tissue.

28. The sensor probe of claim 18, wherein said first end is closed and includes an arcuately shaped surface configured to receive a portion of the tissue.

29. The sensor probe of claim 18, wherein said source and said detector of said electromagnetic energy are distanced from the tissue with the sheath positioned over the tissue.

30. The sensor probe of claim 29, wherein said first end of said sheath comprises first and second cavities which receive said source and said detector, respectively, so as to position said source and said detector away from the tissue over which the sheath covers.

31. The sensor probe of claim 30 additionally comprising coupling medium positioned within said cavities between a medial surface of said sheath and said source and said detector, said coupling medium having a incident of refraction substantially equal to that of the tissue.

32. The sensor probe of claim 18, wherein said source of electromagnetic energy is an optical source and said detector of said electromagnetic energy is an optical detector.

33. The sensor probe of claim 32, wherein said optical source comprises a pair of light emitting diodes which emit optical signals with respective wavelengths in the red and infrared ranges.

34. The sensor probe of claim 32, wherein said optical source and said optical detector are arranged and spaced in axial alignment with each other so as to be on opposite sides of said signals.

35. The sensor probe of claim 18, wherein said sheath comprises a plurality of ventilation holes positioned proximate to said first end.

36. A method of analyzing at least one characteristic of tissue, comprising the steps of:

provciding a source and a detector of electromagnetic energy, said source and detector being interconnected and being separably attached to a retention sheath;

positioning said source of electromagnetic energy against the tissue;

positioning said detector of electromagnetic energy against said tissue;

positioning said retention sheath on a side of said source and detector opposite said tissue with a first end said sheath coupled to said source and detector, said sheath being in a first state in which said first end is separated from a second end by a first distance, said second end being rolled upon itself at least through two revolutions in said first state;

unrolling said second end of said sheath at least through two revolutions from said first state over said tissue and over said source and said detector of electromagnetic energy no surround and secure said source and said detector to said tissue in a second state in which said ends of said sheath spaced apart by a distance substantially greater than said first distance;

transmitting electromagnetic energy through said tissue;

receiving said transmitted electromagnetic energy;

generating a signal indicative of said tissue characteristic;

rolling said sheath off the tissue; and disconnecting said sheath from said source and said detector of electromagnetic energy.

37. The method of claim 36, wherein said transmitting of said electromagnetic energy involves transilluminating the tissue.

38. The method of claim 36, wherein said positioning said source and positioning said detector against said tissue comprises providing a carrier which supports said source and said detector, and folding said carrier over the tissue such that the longitudinal axis of said carrier generally corresponds to the direction of the longitudinal axis of a digit whose tissue is being analyzed.

39. A method for analyzing at least one characteristic of tissue, comprising the steps of:

providing a sensor including at least one source of electromagnetic energy and at least one detector of electromagnetic energy, said sensor being supported by a carrier which has a flexible body;

positioning said carrier against a portion of said tissue to be analyzed with said source of electromagnetic energy positioned against the tissue and said detector of said electromagnetic energy positioned against said tissue;

providing a retention sheath having a tissue receiving end and a rolled end which are integrally connected together;

engaging corresponding elements of a releasable connector so as to connect said carrier to said retention sheath;

unrolling said retention sheath over said tissue and over said carrier so as to surround and secure said carrier to said tissue;

transmitting electromagnetic energy through said tissue;

receiving said transmitted electromagnetic energy;

generating a signal indicative of said tissue characteristic;

rolling said sheath off said tissue; and disconnecting said engaging elements of said releasable connector so as to separate said carrier from said sheath.

* * * * *

UNITED STATES PATENT AND TRADEMARK OFFICE
CERTIFICATE OF CORRECTION

PATENT NO. : 5,452,717

DATED : September 26, 1995

INVENTOR(S) : Branigan et al.

It is certified that error appears in the above-indentified patent and that said Letters Patent is hereby corrected as shown below:

```
Column 10, line 55, change "portion of said tissue" to --portion of the
tissue--
Column 12, line 63, change "medial surface-of" to --medial surface of--
Column 13, line 10, change "sides of said signals." to --sides of said
tissue so as to transilluminate said tissue with optical signals.--
Column 13, line 36, change "energy no surround" to --energy to surround"
Column 13, line 38, change "said sheath spaced" to --said sheath are
spaced--
```

Signed and Sealed this

Thirtieth Day of April, 1996

Attest:

BRUCE LEHMAN

*Attesting Officer*    *Commissioner of Patents and Trademarks*